United States Patent
Thomason

(10) Patent No.: US 9,693,933 B2
(45) Date of Patent: Jul. 4, 2017

(54) OSTOMY POUCH AND PEG TUBE ARRANGEMENT

(71) Applicant: International Business Machines Corporation, Armonk, NY (US)

(72) Inventor: Karl A. Thomason, Austin, TX (US)

(73) Assignee: International Business Machines Corporation, Armonk, NY (US)

( * ) Notice: Subject to any disclaimer, the term of this patent is extended or adjusted under 35 U.S.C. 154(b) by 361 days.

(21) Appl. No.: 13/966,088

(22) Filed: Aug. 13, 2013

(65) Prior Publication Data

US 2015/0051572 A1    Feb. 19, 2015

(51) Int. Cl.
*A61J 15/00*  (2006.01)
*A61F 5/44*   (2006.01)
*A61M 31/00*  (2006.01)

(52) U.S. Cl.
CPC ......... *A61J 15/0026* (2013.01); *A61F 5/4404* (2013.01); *A61J 15/0015* (2013.01); *A61M 31/00* (2013.01)

(58) Field of Classification Search
CPC .... A61J 15/00; A61J 15/0015; A61J 15/0019; A61J 15/0023; A61J 15/0026–15/0096; A61F 5/0003; A61F 5/0013; A61F 5/0036; A61F 5/0069; A61F 5/0073; A61F 5/0076; A61F 5/0079; A61F 5/44; A61F 5/445; A61F 5/448; A61F 13/02; A61F 5/443
USPC ... 604/8, 317, 327, 332, 333, 334, 335, 336, 604/345, 533, 534, 540, 910, 337–344
See application file for complete search history.

(56) References Cited

U.S. PATENT DOCUMENTS

| | | | | |
|---|---|---|---|---|
| 3,825,005 A | * | 7/1974 | Fenton | A61F 5/4407 315/239 |
| 5,662,268 A | | 9/1997 | Katzenberger | |
| 5,951,532 A | * | 9/1999 | Olsen | A61F 5/445 604/332 |
| 8,029,462 B2 | | 10/2011 | Chu | |
| 8,057,429 B2 | | 11/2011 | Nath | |
| 2003/0187424 A1 | * | 10/2003 | Chu | A61J 15/0015 604/537 |
| 2004/0116894 A1 | | 6/2004 | Delegge | |
| 2010/0160875 A1 | * | 6/2010 | James | 604/319 |

FOREIGN PATENT DOCUMENTS

DE    697121461 T2    9/1998

OTHER PUBLICATIONS

Torek, Franz, "The Operative Treatment of Caracinoma of the Esophagus," Ann.Surgery, vol. LXI, No. 4, Apr. 1915, pp. 385-405.

* cited by examiner

*Primary Examiner* — Kami A Bosworth
(74) *Attorney, Agent, or Firm* — Anthony V. S. England; Ingrid Foerster

(57) ABSTRACT

For a person who has a percutaneous endoscopic gastrostomy ("PEG") tube and an esophagus stoma, an ostomy pouch is provided, where the pouch forms an inlet connected to the esophagus stoma and an outlet connected to one end of a interconnecting tube. An opposing end of the interconnecting tube is connected to the PEG tube, so that when the person consumes matter by mouth, the matter flows out the stoma, through the ostomy pouch, the interconnecting tube and the PEG rube, and into the stomach.

16 Claims, 4 Drawing Sheets

OSTOMY POUCH AND PEG TUBE ARRANGEMENT

FIELD OF THE INVENTION

The present invention relates to personalized healthcare. Specifically, the present invention relates to delivery of matter from an ostomy pouch for the swallowing impaired.

BACKGROUND

A person (hereafter referred to as an "ostomate") whose esophagus has been detached from their stomach and routed through an opening (a "stoma") is unable to eat and drink orally. Ostomates must nourish themselves using a percutaneous endoscopic gastrostomy ("PEG") tube, which is a tube connected to the stomach from outside the body.

SUMMARY

According to an embodiment of the invention, a system is provided for a person who has a percutaneous endoscopic gastrostomy ("PEG") tube and an esophagus stoma. The system includes an ostomy pouch forming an inlet connected to the esophagus stoma and an outlet connected to one end of a interconnecting tube, wherein an opposing end of the interconnecting tube is connected to the PEG tube, so that when the person consumes matter by mouth, the matter flows out the stoma, through the ostomy pouch, the interconnecting tube and the PEG tube, and into the stomach.

According to an embodiment of the invention, a system is provided for a person who has a PEG tube and an esophagus stoma, wherein the system includes an ostomy pouch forming an inlet at a baseplate connected to the pouch, wherein the baseplate and inlet are shaped to fit over the stoma and the pouch forms an outlet attached to a pouch outlet connector, the outlet being located in the pouch such that when the person is in an upright position and the pouch inlet is fixed to the stoma with a major portion of the pouch extending downward, the outlet of the pouch is located below the inlet, wherein the pouch outlet connector has a shape that matches a first connector on a first end of an interconnecting tube and the interconnecting tube has a second connector on an opposing, second end, the second interconnecting tube connector having a shape that matches a connector of the PEG tube, so that with the pouch inlet fixed to the stoma, the pouch outlet connector fixed to the first interconnecting tube connector and the second interconnecting tube connector fixed to the connector of PEG tube, when the person consumes matter by mouth, the matter consumed flows out of the stoma, through the ostomy pouch, the interconnecting tube and the PEG tube, and into the stomach.

According to an embodiment of the invention, a method is provided for an ostomate to use an ostomy pouch. The method comprises connecting an inlet of the ostomy pouch to an esophagus stoma of a user, fixing an outlet of the ostomy pouch to a first end of an interconnecting tube and connecting a second, opposing end of the interconnecting tube to an external end of a percutaneous endoscopic gastrostomy ("PEG") tube, where the PEG tube provides a connection to the user's stomach, so that matter consumed by mouth flows through the ostomy pouch, the interconnecting tube and PEG tube, and into the stomach.

Other embodiments of the invention are disclosed and may be claimed, including a method for modifying an ostomy pouch.

BRIEF DESCRIPTION OF DRAWINGS

The novel features believed characteristic of the invention are set forth in the appended claims. The invention itself, however, as well as a preferred mode of use, further objectives and advantages thereof, will best be understood by reference to the following detailed description of an illustrative embodiment when read in conjunction with the accompanying drawings, wherein:

DETAILED DESCRIPTION

Because of their medical condition, ostomates lose or have a greatly limited ability to enjoy the taste of foods and beverages. Reattaching the esophagus to the stomach may not be an option. Even if this is an option, the person may not wish to risk undergoing reattachment surgery.

While the ostomate may not be prohibited from eating and drinking orally, anything that is taken orally will be discarded immediately through the bottom of the esophagus and out the stoma, which is typically below the shoulders. An ostomy pouch is attached over this stoma to catch and store salvia and anything else swallowed by the ostomate. Drinking water or enjoying a cup of coffee will quickly fill the bag which must be emptied. It is often impractical for ostomates to empty a stoma bag (e.g., in the middle of a meeting). Further, since the stoma bag is worn under clothes, the risk of the stoma bag bursting and messing the clothes is a real issue.

Through embodiments of the present invention, the ostomate may taste beverages and liquid foods and have them enter the body through the stomach. (Liquids and flowable food having only suitably small particulates, such as particulates less than 2 mm in size, for example, may be referred to herein as "matter.") This is particularly advantageous with regard to drinking water, because it allows quenching thirst and hydrating the body at the same time. Further, embodiments of the inventions provide a system that can be worn under clothing, allowing ostomates to drink normally without drawing attention to their condition.

Figure 1:
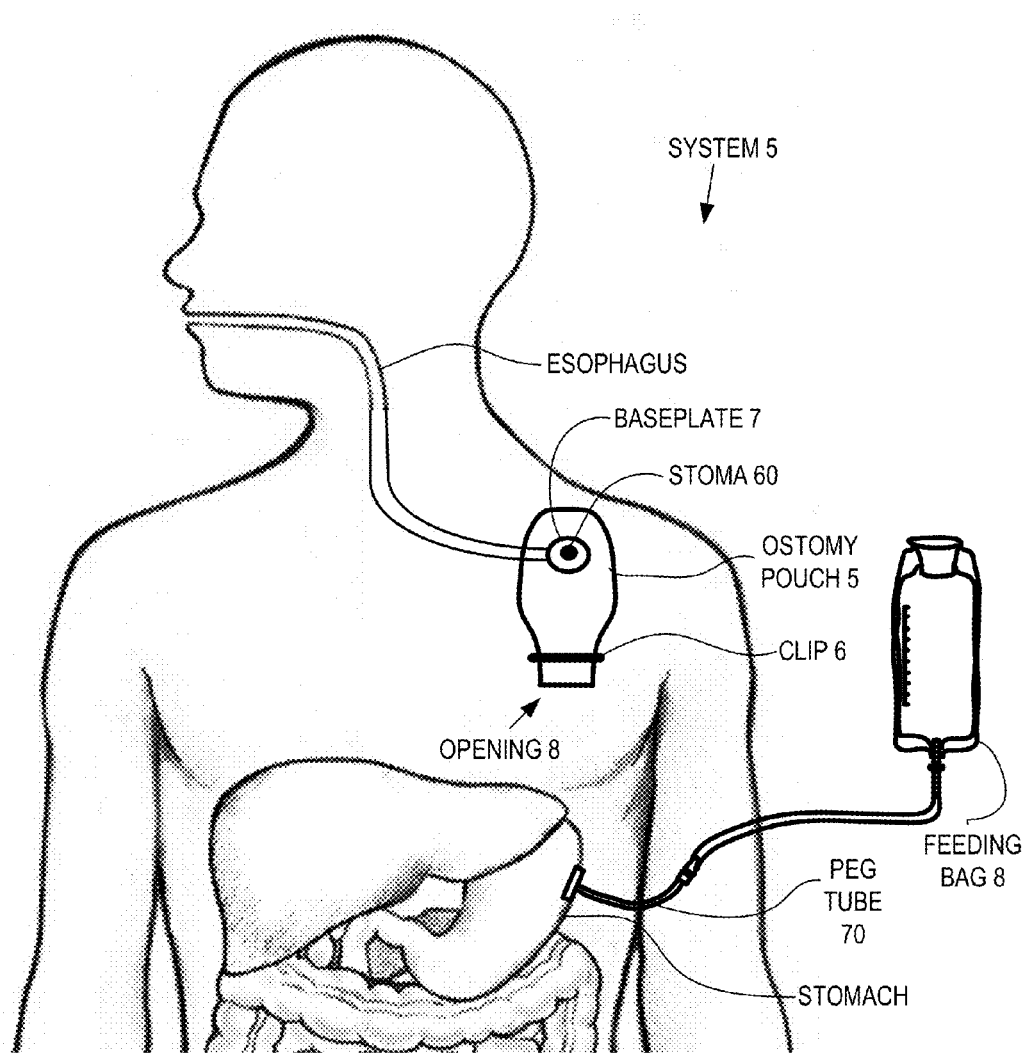
FIG. 1 illustrates an ostomy pouch and feeding bag, according to prior art.

Referring to FIG. 1, a prior art ostomy pouch 5 is depicted. An ostomate attaches the pouch 5 to their stoma 60 by adhering stoma baseplate 7 around stoma 60. The ostomate closes the bottom of the pouch 5 with clip 6. Pouch 5 is used just to collect saliva and anything else that is swallowed.

In order to nourish themselves, an ostomate generally attaches a syringe or bag 8 (much like an IV bag) directly to their PEG tube 70. As shown, bag 8 is connected to peg tube 70 on the bottom end of bag 8 but not connected to stoma 60. The ostomate pours liquid into bag 8, which is then transferred to the stomach via PEG tube 70. The ostomate does not taste anything, since the liquid does not enter the mouth.

Figure 2:
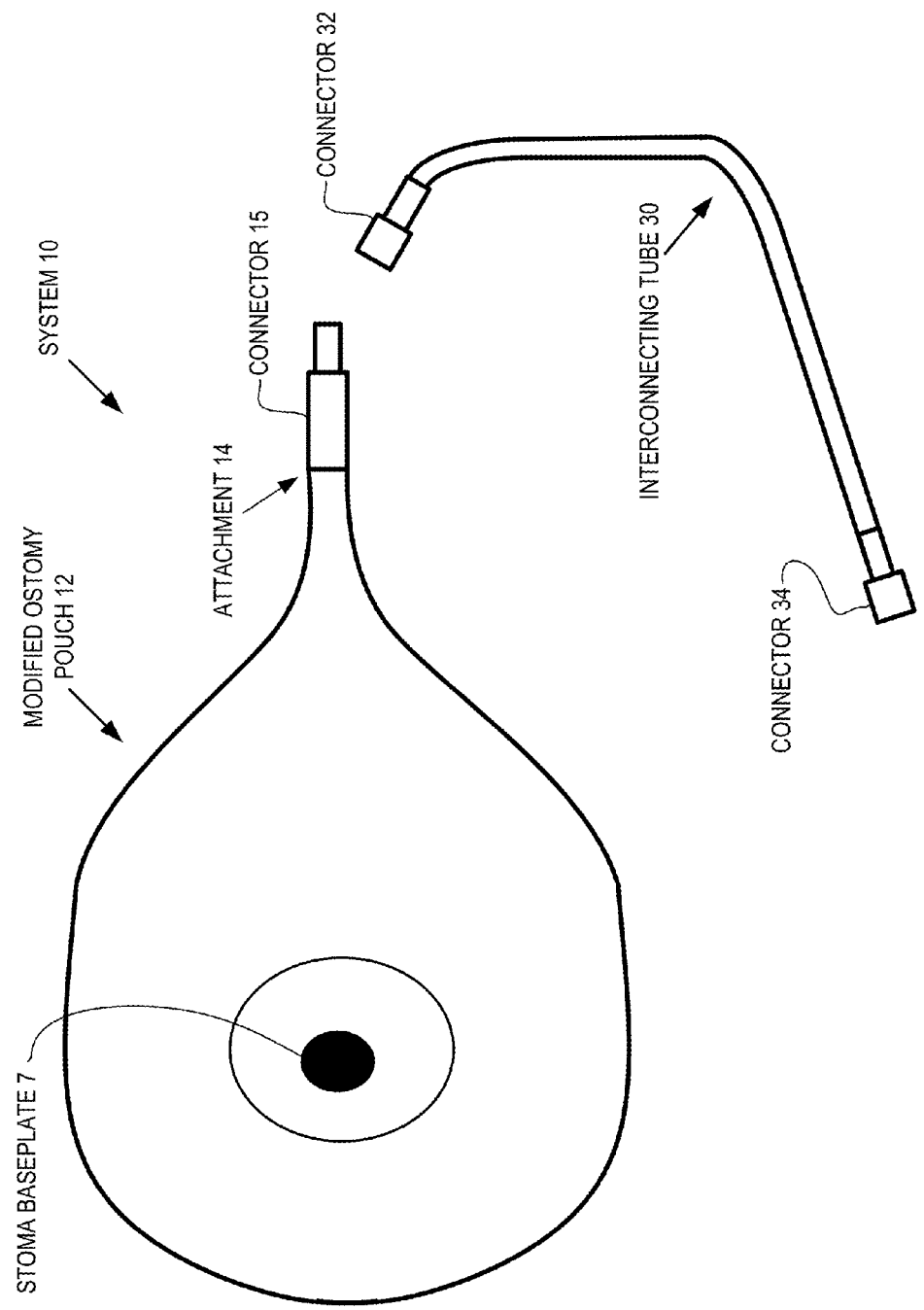
FIG. 2 illustrates a system in which an ostomy pouch is connected to a PEG tube, according to embodiments of the invention.

With reference to the FIG. 2, a system 10 is shown, which is for transferring fluids, such as water, coffee, and other non-particle liquids out an ostomate's stoma and into the ostomate's stomach via specifically designed or adapted ostomy pouch 12 and interconnecting tube 30 connecting pouch 12 to the stomach, according to embodiments of the present invention. Tube 30 may be sized according to maximum allowable size of particulates in matter that is consumed. For example, for flowable food having a 1/16 inch maximum particulate size limit, tube 30 may be 1/2 inch. Pouch 12 inlet and outlet may likewise be sized according to maximum allowable size of particulates.

Figure 3:
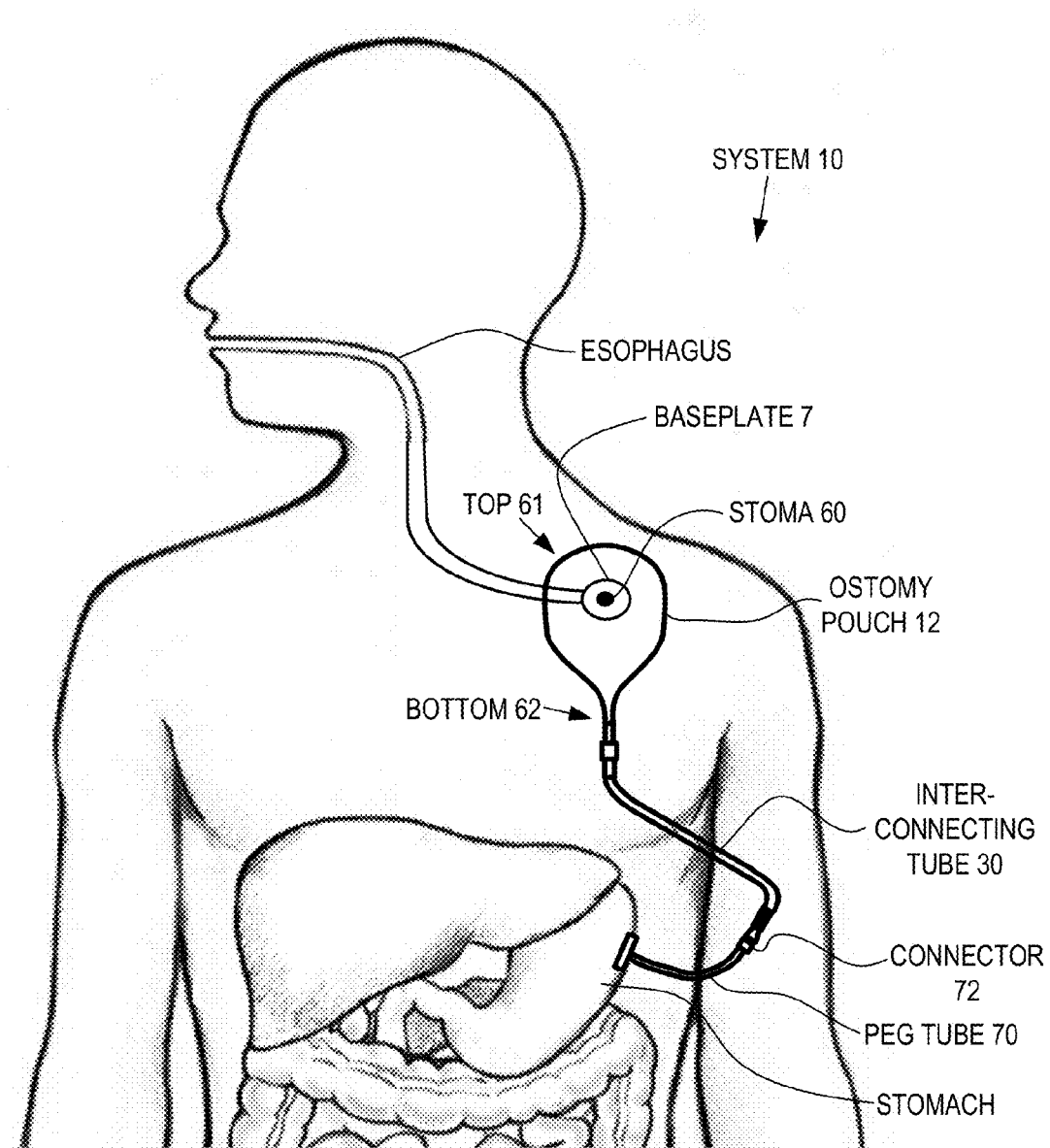
FIG. 3 illustrates the system of FIG. 2 as applied to an ostomate, according to embodiments of the invention.

Referring now also to FIG. 3, system 10 is shown attached to an ostomate, according to embodiments of the present invention, wherein ostomy pouch 12 is connected to an esophagus stoma 60 of a user, who is an ostomate. Pouch 12 has an outlet at or near the bottom 62 connected to one end of a interconnecting tube 30, wherein the other end of the interconnecting tube 30 is connected to one end of a PEG tube 70 outside the user's body, where PEG tube 70 is connected at the other end to the user's stomach, so that the user may consume liquids and suitable foods by mouth, which flow out of the ostomy pouch, through interconnecting tube 30 and PEG tube 70 and into the stomach.

Modified ostomy pouch 12 attaches to the ostomate like a normal ostomy pouch by stoma baseplate 7, which is located near the top 61 of pouch 12, such as within 20% of the pouch length from the top. The ostomate attaches connector 15, which provides an outlet located at or near the bottom 62 of ostomy pouch 12, to interconnecting tube 30 using connector 32 on a first end of tube 30. The outlet may be within 20% of the pouch length from the pouch bottom, for example. In FIG. 3, the outlet is at the bottom. Interconnecting tube 30 is connected to PEG tube 70 using connector 34 on the other end of tube 30. All liquids taken in orally will flow into the ostomy pouch 12, through tube 30, through PEG tube 70, and into ostomate's stomach. This allows the user to taste and enjoy liquid taken through the mouth.

It should be appreciated from the foregoing that in embodiments of the present invention, a system for a person who has a PEG tube 70 and an esophagus stoma 60 includes an ostomy pouch 12 forming an net at a baseplate 7 connected to the pouch, where a shape of baseplate 7 fits over stoma 60. The pouch also forms an outlet at connector 15, wherein the outlet is located in the pouch such that when the person is in an upright position and the net is fitted to stoma 60 with a major portion of pouch 12 extending downward, the outlet of pouch 12 is located below the inlet. Connector 15 has a shape that matches a first connector 32 on a first end of an interconnecting tube 30 for connecting the pouch outlet to PEG tube 70. A second connector 34 on an opposing, second end of interconnecting tube 30 has a shape that matches a connector of the PEG tube. With the pouch inlet fitted to stoma 60, the pouch outlet connector 15 fitted to the first interconnecting tube connector 32 and the second interconnecting tube connector 34 fitted to the connector of PEG tube 70, when the person consumes matter by mouth, the matter consumed flows out of stoma 60, through ostomy pouch 12, interconnecting tube 30 and PEG tube 70, and into the stomach.

Figure 4:
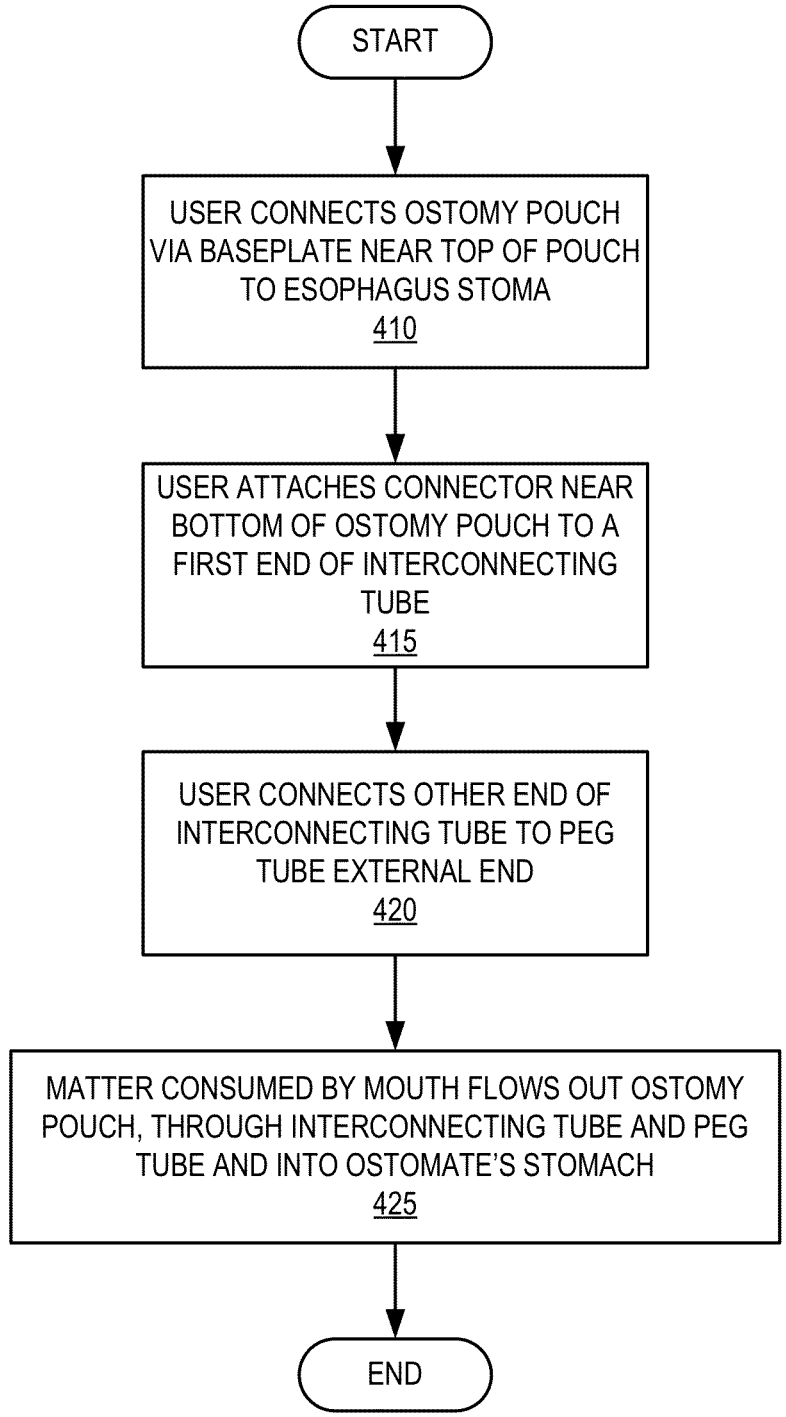
FIG. 4 illustrates a process by which an ostomate uses the system of FIGS. and 3.

Referring now to FIG. 4 together with FIGS. 2 and 3, a method for using ostomy pouch 12 is illustrated, according to embodiments of the invention. In action 410, a user connects ostomy pouch 12, via baseplate 7 near top 61 of pouch 12, to an esophagus stoma 60 of the user, who is an ostomate. In action 415, the user attaches a connector 15 of ostomy pouch 12, which is at or near bottom 62, to interconnecting tube 30 using connector 32 on a first end of tube 30. In action 420, the user connects the other end of the interconnecting tube 30 to an end of a PEG tube 70 outside the user's body, where PEG tube 70 is connected at the other end to the user's stomach. With pouch 12 connected via tube 30 to tube 70, the user may, in action 425, consume liquids and suitable foods by mouth, which flow out of ostomy pouch 12, through interconnecting tube 30 and PEG tube 70 and into the stomach.

As previously described, a prior art ostomy pouch 5 has an opening 8 at an end opposite baseplate 7, where opening 8 may be held closed by clip 6, as shown in FIG. 1. Ostomy pouch 12 (FIG. 2) differs from prior art pouch 5 at least in that pouch 12 is adapted to connect to interconnecting tube 30. In embodiments of the present invention, pouch 12 may be molded to include connector 15 for connecting to tube 30. Alternatively, a method for modifying pouch 5, according to embodiments of the present invention, includes attaching connector 15, as shown in modified pouch 12 (FIG. 2), to opening 8 (FIG. 1) in order to provide an outlet. In order for the attachment to be liquid tight, the end of connector 15 that is inserted in opening 8 may be only slightly smaller than the diameter of the opening 8. Alternatively, opening 8 (FIG. 1) may be flattened and wrapped around connector 15, as is shown in FIG. 2. Attachment 14 (FIG. 2) may be via adhesive or a fastener, such as an elastic band, hose clamp, or cable tie (also commonly referred to as a hose tie, zip tie or tie-wrap).

A hose clamp is a known device. There are a variety of types of hose clamps. One type is the screw clamp, for example, which may include a strip into which a screw thread pattern has been cut or pressed. The strip has a head on one end, which includes a slot and a captive screw, such that when the other end of the strip is fed into the slot, the strip is held between one face of the strip and the captive screw. The screw and thread pattern acts as a worm drive for tightening and loosening the band around connector 15, which seals the material at opening 8 of pouch 5 around connector 15. Other types of hose clamps are known, such as spring type and wire type.

A cable tie is a known device commonly including a long narrow strip of nylon having asymmetrical teeth on one face, wherein the teeth gently slope on one edge and more steeply slope on the other. The strip has a head on one end, which includes a slot and a flexible pawl. When the other end of the cable tie strip is inserted through the slot, the non-teeth face of the strip at the head is held against the non-teeth face of the inserted end and the pawl slides over the gently sloped edge of each tooth on the opposite face and then into the depressions between teeth as the strip is further inserted, such that the pawl catches against the steeply sloped edge of each tooth it contacts, thereby locking the strip against the contacting tooth and preventing removal of the strip from the head in the reverse of the inserted direction. By pulling on the end of the strip inserted into the head-end, the strip is pulled irreversibly tighter around connector 15, which seals the material at opening 8 of pouch 5 around connector 15.

While this specification contains many specifics, these should not be construed as limitations on the scope of the invention or of what can be claimed, but rather as descriptions of features specific to particular implementations of the invention. Certain features that are described in this specification in the context of separate implementations can also be implemented in combination in a single implementation. Conversely, various features that are described in the context of a single implementation can also be implemented in multiple implementations separately or in any suitable sub combination. Moreover, although features can be described above as acting in certain combinations and even initially claimed as such, one or more features from a claimed combination can in some cases be excised from the combination, and the claimed combination can be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing can be advantageous. Moreover, the separation of various system components in the implementations described above should not be understood as requiring such separation in all implementations, and it should be understood that the described program components and systems can generally be integrated together in a single software product or packaged into multiple software products.

Those skilled in the art having read this disclosure will recognize that changes and modifications may be made to the embodiments without departing from the scope of the present invention.

It should be appreciated that the particular implementations shown and described herein are illustrative of the invention and its best mode and are not intended to otherwise limit the scope of the present invention in any way. Other variations are within the scope of the following claims.

The actions recited in the claims can be performed in a different order and still achieve desirable results. Likewise, the processes depicted in the accompanying figures do not necessarily require the particular order shown, or sequential order, to achieve desirable results. In certain implementations, multitasking and parallel processing can be advantageous.

Benefits, other advantages, and solutions to problems have been described above with regard to specific embodiments. However, the benefits, advantages, solutions to problems, and any element(s) that may cause any benefit, advantage, or solution to occur or become more pronounced are not to be construed as critical, required, or essential features or elements of any or all the claims.

As used herein, the terms comprises, comprising, or any other variation thereof, are intended to cover a non-exclusive inclusion, such that a process, method, article, or apparatus that comprises a list of elements does not include only those elements but may include other elements not expressly listed or inherent to such process, method, article, or apparatus. Further, no element described herein is required for the practice of the invention unless expressly described as essential or critical.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

In additional embodiments a database administrator or system administrator may set limits as described herein above. Multiple soft limits can be set as well. Further, it should be understood that there may be different limits for different database objects depending on importance or similar criteria. Similarly, there may be different limits for different types of transactions, such as, for example, after a first soft limit is encountered updates are still allowed for account transfer transactions but are not allowed for change-of-address transactions, etc.

What is claimed is:

1. A system comprising:
    a PEG tube;
    an ostomy pouch; and
    an interconnecting tube, wherein the ostomy pouch and the interconnecting tube provide a passage having an inlet and an outlet, the passage inlet being adapted to fit an esophagus stoma, wherein the ostomy pouch forms an inlet providing the passage inlet and the ostomy pouch forms an ostomy pouch outlet, the ostomy pouch outlet having a connection to one end of the interconnecting tube, wherein the interconnecting tube has an opposing end of the interconnecting tube that forms the passage outlet and has a connection to an inlet of the PEG tube, wherein the passage outlet faces the PEG tube inlet and is aligned with the PEG tube inlet, and wherein the ostomy pouch outlet connection to the interconnecting tube is above an outlet of the PEG tube, so that when a person consumes matter by mouth, the matter flows out the stoma, through the ostomy pouch, the interconnecting tube and the PEG tube, and into the person's stomach.

2. The system of claim 1, wherein when the ostomy pouch is connected to the stoma, the ostomy pouch outlet is connected to the interconnecting tube below the ostomy pouch inlet.

3. The system of claim 1, wherein the ostomy pouch has a top and a bottom and the ostomy pouch outlet is near the bottom of the pouch.

4. The system of claim 1, wherein the ostomy pouch has a top and a bottom and the ostomy pouch inlet is near the top of the pouch.

5. The system of claim 1, wherein the ostomy pouch includes a baseplate connected to the ostomy pouch inlet.

6. The system of claim 1, wherein the ostomy pouch outlet connection to the interconnecting tube includes a connector.

7. The system of claim 6, wherein the connector is attached to the ostomy pouch outlet via adhesive.

8. The system of claim 6, wherein the connector is attached to the ostomy pouch outlet via a cable tie.

9. The system of claim 6, wherein the connector is attached to the ostomy pouch outlet via a hose clamp.

10. The system of claim 1, wherein the interconnecting tube includes connectors at the ends of the interconnecting tube.

11. The system of claim 10, wherein the ostomy pouch includes an outlet connector attached to the ostomy pouch outlet and the ostomy pouch outlet connector has a shape that matches one of the connectors of the interconnecting tube.

12. A system comprising:

a PEG tube;

an ostomy pouch forming an inlet at a baseplate connected to the ostomy pouch, wherein the baseplate and inlet of the ostomy pouch are shaped to fit over an esophagus stoma and the ostomy pouch forms an outlet attached to a ostomy pouch outlet connector, the outlet of the ostomy pouch being located in the ostomy pouch such that when a person is in an upright position and the ostomy pouch inlet is fixed to the stoma with a major portion of the ostomy pouch extending downward, the outlet of the ostomy pouch is located below the ostomy pouch inlet, wherein the ostomy pouch outlet connector has a shape that matches a first connector on an inlet of an interconnecting tube and the interconnecting tube has a second connector on an outlet of the interconnecting tube, the second interconnecting tube connector having a shape that matches a connector on an inlet of the PEG tube, wherein the second interconnecting tube connector and the connector on the inlet of the PEG tube inlet are configured such that with the second interconnecting tube connector connected to the connector on the PEG tube inlet, the interconnecting tube outlet faces the PEG tube inlet and is aligned with the PEG tube inlet, so that with the ostomy pouch inlet fixed to the stoma, the ostomy pouch outlet connector fixed to the first interconnecting tube connector and the second interconnecting tube connector fixed to the connector of the PEG tube, when the person consumes matter by mouth, the matter consumed flows out of the stoma, through the ostomy pouch, the interconnecting tube and the PEG tube, and into the person's stomach.

13. The system of claim 12, wherein the ostomy pouch outlet connector is attached to the ostomy pouch outlet via adhesive.

14. The system of claim 12, wherein the ostomy pouch outlet connector is attached to the ostomy pouch outlet via a cable tie.

15. The system of claim 12, wherein the ostomy pouch outlet connector is attached to the ostomy pouch outlet via a hose clamp.

16. The system of claim 12, wherein the ostomy pouch outlet connector is attached to the interconnecting tube above an outlet of the PEG tube.

* * * * *